United States Patent
Bridges et al.

(10) Patent No.: US 7,348,466 B2
(45) Date of Patent: Mar. 25, 2008

(54) SOLVENT EXTRACTION (75) Inventors: Joseph P. Bridges, Corpus Christi, TX (US); Solon B. Williams, Kingwood, TX (US); Byron B. Unterbrink, Corpus Christi, TX (US)

(73) Assignee: Equistar Chemicals, LP, Houston, TX (US)

( * ) Notice: Subject to any disclaimer, the term of this patent is extended or adjusted under 35 U.S.C. 154(b) by 569 days.

(21) Appl. No.: 11/104,990

(22) Filed: Apr. 13, 2005

(65) Prior Publication Data

US 2006/0235257 A1    Oct. 19, 2006

(51) Int. Cl.
C07C 7/07    (2006.01)
C07C 7/10    (2006.01)

(52) U.S. Cl. .................. 585/809; 585/807; 585/810; 585/833; 585/860

(58) Field of Classification Search ................ 585/809, 585/801, 833, 860
See application file for complete search history.

(56) References Cited

U.S. PATENT DOCUMENTS

| | | | | |
|---|---|---|---|---|
| 2,600,106 | A * | 6/1952 | Garrett | 203/41 |
| 2,993,841 | A | 7/1961 | Sarno | 202/39.5 |
| 3,436,438 | A | 4/1969 | Takao et al. | 260/681.5 |
| 4,134,795 | A | 1/1979 | Howat, III | 203/53 |
| 4,277,315 | A * | 7/1981 | Volkamer et al. | 203/51 |
| 4,348,260 | A * | 9/1982 | Hokari et al. | 203/9 |
| 6,395,953 | B1 * | 5/2002 | Koga et al. | 585/833 |

* cited by examiner

Primary Examiner—Tam M. Nguyen
(74) Attorney, Agent, or Firm—Roderick W. MacDonald (57) ABSTRACT In a method for the solvent extraction of butadiene from a mixture of hydrocarbons having four carbon atoms per molecule, which method inherently produces tars, the extraction process is operated with a tar loading level, relative to the solvent employed, of no more than about 1.6 wt. %.

11 Claims, 5 Drawing Sheets

SOLVENT EXTRACTION

BACKGROUND OF THE INVENTION

1. Field of the Invention

This invention relates to the solvent extraction of butadiene from a mixture of hydrocarbons having four carbon atoms per molecule ($C_4$'s).

2. Description of the Prior Art

Thermal cracking of hydrocarbons is a petrochemical process that is widely used to produce individual olefin products such as ethylene, propylene, butenes, butadiene, and aromatics such as benzene, toluene, and xylenes. In such olefin production plants, a hydrocarbonaceous feedstock such as ethane, naphtha, gas oil, or other fractions of whole crude oil is mixed with steam which serves as a diluent to keep the hydrocarbon molecules separated. This mixture, after preheating, is subjected to severe hydrocarbon thermal cracking at elevated temperatures of about 1,450 to 1,550° Fahrenheit (F.) in a pyrolysis furnace (steam cracker or cracker).

The cracked product effluent from the pyrolysis furnace contains hot, gaseous hydrocarbons, both saturated and unsaturated, of great variety from 1 to 35 carbon atoms per molecule ($C_1$ to $C_{35}$). This furnace product is then subjected to further processing to produce, as products of the olefin plant, various, separate product streams of high purity, e.g., molecular hydrogen, ethylene, and propylene. After separation of these individual streams, the remaining cracked product contains essentially hydrocarbons with four carbon atoms per molecule ($C_4$'s) and heavier. This remainder is fed to a debutanizer wherein a crude $C_4$ stream is separated as overhead while a $C_5$ and heavier stream is removed as a bottoms product.

The crude $C_4$ stream has a variety of compounds such as n-butane, isobutane, 1-butene, 2-butenes (cis and trans), isobutylene, butadiene (1,2- and 1.3-), vinyl acetylene, and ethyl acetylene, all of which are known to boil within a narrow range, U.S. Pat. No. 3,436,438. Further, some of these compounds can form an azeotrope. Crude $C_4$'s are, therefore, known to be difficult to separate by simple distillation.

The crude $C_4$ fraction, after removal of acetylenes, normally goes to a butadiene extraction unit for separation of butadiene from the fraction. Thereafter, isobutylene can be removed by, for example, reaction with methanol to form methyl-tert-butyl ether (mtbe). Butenes can then be distilled from the mtbe, and 1-butene separated from 2-butenes by simple distillation.

The dominating process for separating butadiene from crude $C_4$'s is known technically as "fractional extraction," but is more commonly referred to as "solvent extraction" or "extractive distillation." However it is termed, this process employs an aprotic polar compound that has a high complexing affinity toward the more polarizable butadiene than other olefins in the crude $C_4$ stream. Known solvents for this process include acetonitrile, dimethylformamide, furfural, N-methyl-2-pyrrolidone, acetone, dimethylacetamide, and the like. This process and the solvents used therein are well known, U.S. Pat. Nos. 2,993,841 and 4,134,795. It is equally well known that this type of process inherently generates internally tars (tar) that, if not controlled, can affect the quality of the butadiene separated as a product of the process, and even plug equipment, thereby causing an expensive and time consuming shut down and clean out of the plant. Accordingly, there is continuous effort in the industry to which this process pertains to find solvents that reduce tar formation and deposition in equipment.

This invention takes a different tack from industry in addressing the control of tar formation and deposition in a butadiene extraction unit, in that it controls tars without changing the known solvents used in such a process.

Heretofore, in butadiene extraction plants such as that shown in FIGS. 1-4 herein below, wherein a primary solvent and a secondary solvent were employed, it was dogma that some tar content suspended in the solvent mixture (primary and secondary) circulating in the system was necessary to keep tar formation and deposition at a minimum in the system as a whole. Accordingly, operators of such extraction plants were required without fail to maintain in the solvent mixture a tar level (load) of not less than 2 weight percent (wt. %) and a total content of tars plus secondary solvent of 5 wt. %, both weight percents being based on the total weight of the solvent mixture plus tar circulating in the system. For example, the unswerving operating specifications for this type of plant known as the Nippon-Zeon design required the tar level to be 2 wt. % minimum and the combined tar and secondary solvent level to be 5 wt. %, i.e., 2 wt. % tar and 3 wt. % secondary solvent, the remainder being 95 wt. % primary solvent. These design criteria were slavishly followed by operators of such plants.

SUMMARY OF THE INVENTION

It has been found that, at the tar levels heretofore required by the industry as necessary, tar formation control (minimization) was not achieved. It was found that at the above tar and tar/secondary solvent levels deemed necessary by industry, tar formation and deposition were not controlled. In actuality, it has been found that at the levels dictated by industry, the tar present begat more tar instead of controlling tar formation.

In accordance with this invention, tar formation and deposition is controlled by deliberately maintaining the level of tars in the butadiene extraction system substantially below that which was considered necessary in the industry to prevent tar formation and deposition, i.e., not greater than about 1.6 wt. % in the solvent (primary alone or primary plus secondary) plus tar system.

It was surprisingly found that with the tar loading of this invention, the extraction system as a whole became self-cleaning in that the rate of formation of tars in the system actually decreased, and existing tar deposits were reduced.

It was further found that an essentially self-cleaning extraction system, with respect to tars formed therein, is established when the tar level is maintained at no more than about 1.6 wt. % and the total content of tars plus secondary solvent is at the same time maintained at a level of less than 5 wt. %, both wt. % based on the total weight of the solvents plus tar present and circulating in the system.

Finally, it was found that such tar and tar/secondary solvent loadings could be achieved in such a system only by alteration of the solvent reclamation system that is normally employed in such plants.

DETAILED DESCRIPTION OF THE INVENTION

Although this invention is discussed, for sake of clarity and brevity, in respect of a Nippon-Zeon type design, it is to be understood that this invention can be employed in other designs so long as the tar minimization advantages of this invention are achieved.

Figure 1:
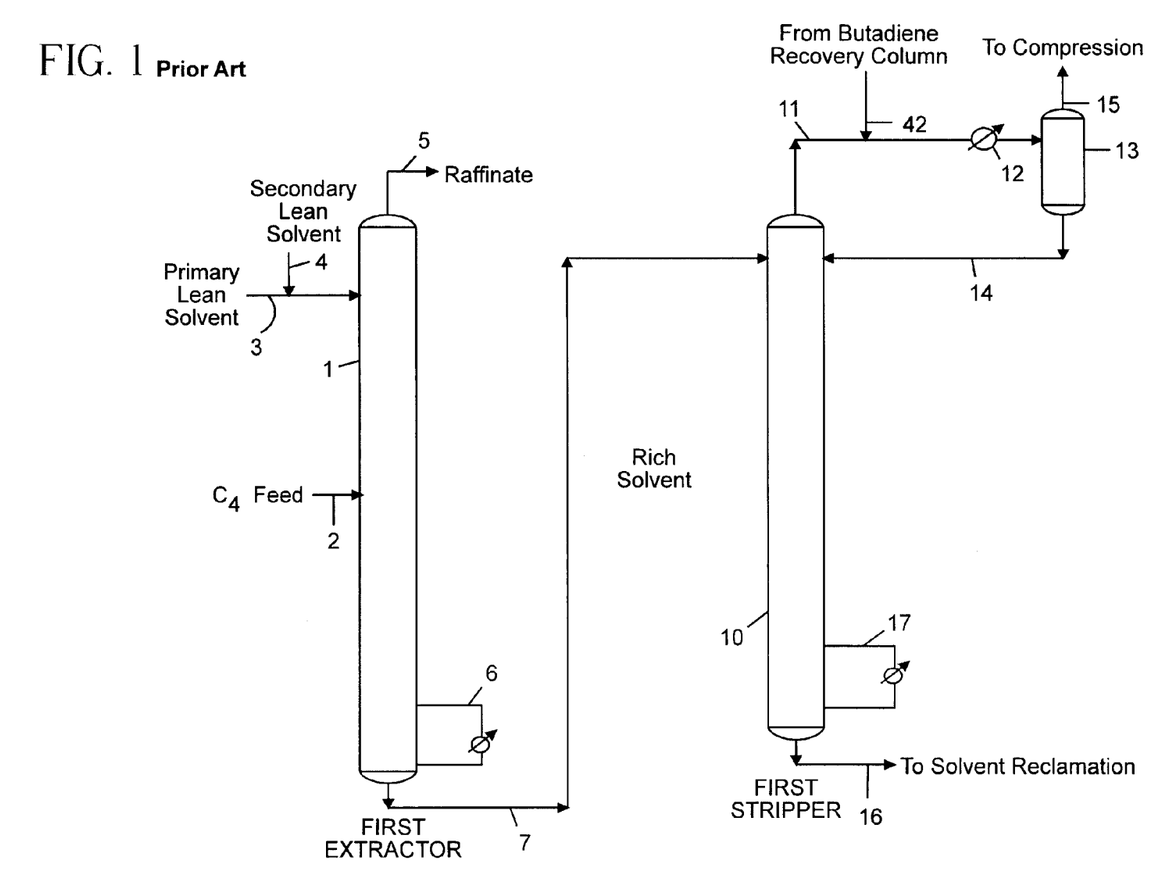
FIG. 1 shows a first extractor circuit for a commercial design that employs primary and secondary solvents.

FIG. 1 shows the first section of the extraction unit to contain a first reboiled butadiene extractor 1 to which is fed crude $C_4$ feedstock 2. Feed 2 is typically first passed into a reboiled vaporizer drum (not shown), and then passed from that drum into extractor 1 at one or more points along the height of that extractor. Lean (essentially $C_4$ free) solvent 3 is introduced into tower 1 above the point(s) of introduction of feed 2 so that the denser, descending solvent 3 can counter currently contact the feed 2 which is rising inside tower 1. Solvent 3 extracts butadiene from feed 2 in known manner. Solvent 3 contains tars, but essentially no butadiene. Solvent 3 is the primary solvent present in the system in that it is present in a major amount. A secondary lean solvent 4 can be mixed with primary solvent 3 in a minor amount, e.g., primary solvent equal to or greater than 50 wt. %, and secondary solvent less than 50 wt. %, based on the total weight of the combined solvents. Solvents 3 and 4 contain tars, but essentially no butadiene.

Heretofore, the prior art deliberately and rigorously maintained the combination of solvents 3 and 4 at a tar loading of not less than 2 wt. % based on the total weight of the solvent combination plus tar loading. By this invention this tar loading is not to exceed about 1.6 wt. %. The combination of solvents 3 and 4 plus tars was heretofore just as rigorously maintained by the prior art at a secondary solvent 4 plus tars loading of not less than 5 wt. %. By this invention this secondary solvent and tar loading is less than 5 wt. %. All wt. % are based on the total weight of solvents 3 and 4 plus tars.

Extractor 1 has at its upper end a conventional reflux circuit that is not shown for sake of clarity but is like that of stripper 10. Raffinate 5 ($C_4$ feed 2 essentially minus its butadiene content) is removed from this circuit for further processing elsewhere. Tower 1 has a conventional reboiler loop 6 for heating the tower.

Bottoms 7 from tower 1 is a mixture of butadiene and solvent(s) and are passed to first reboiled stripper 10 to separate butadiene from solvent. Primarily butadiene, after separation from the solvent, is recovered as overhead from tower 10 in line 11 and enters a conventional reflux circuit composed of at least one heat exchanger 12 and reflux drum 13. Liquid reflux is returned to tower 10 by way of line 14, while a vapor stream rich in butadiene is recovered in line 15 for transport to a compression step shown in FIG. 2.

Bottoms 16 from tower 10 is primarily lean solvent (primary and secondary) and tars that have been formed in the extraction system, of which at least part is removed for reclamation and reuse in the extraction system as lean solvent.

Figure 2:
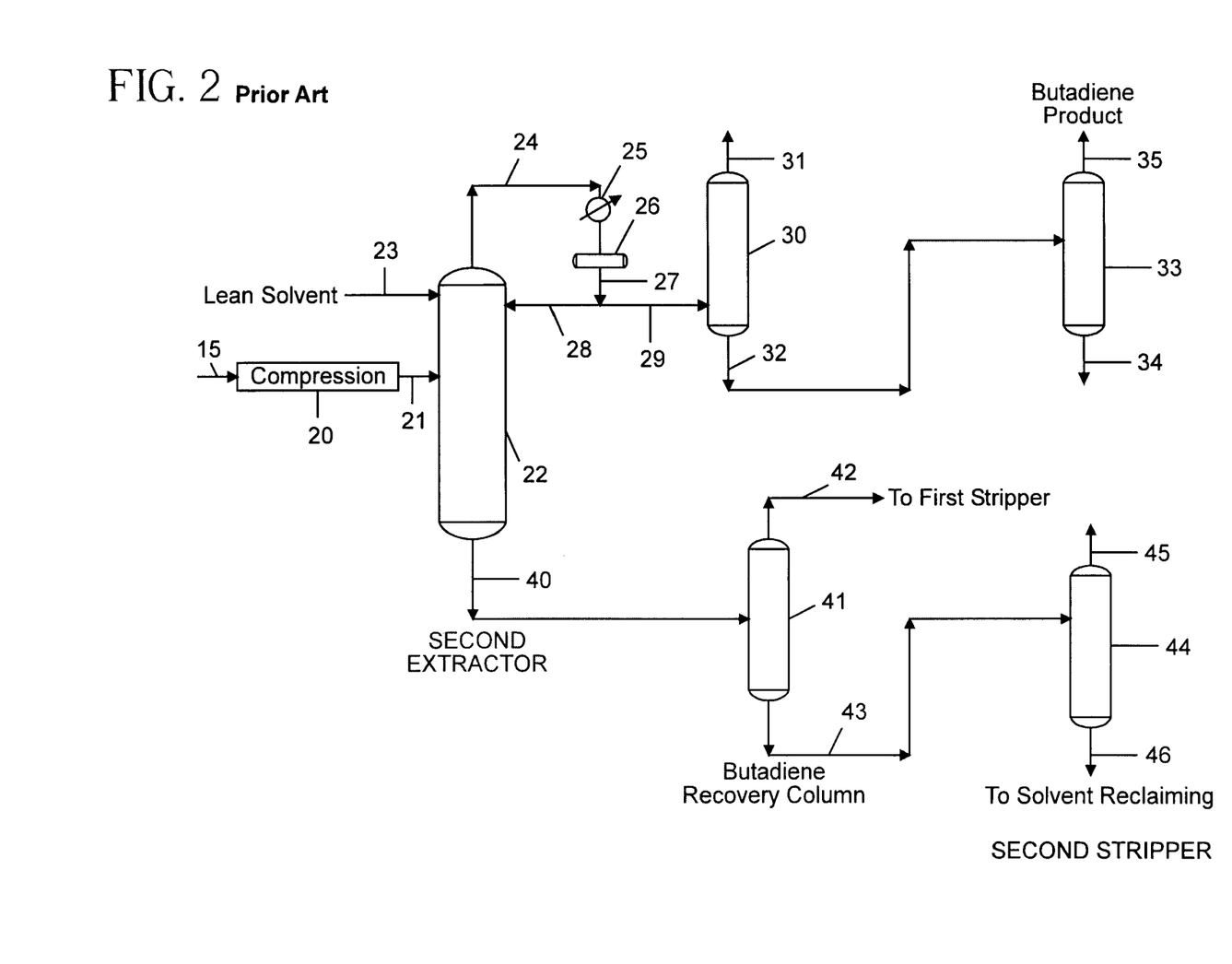
FIG. 2 shows a second extractor circuit that is normally combined with the circuit of FIG. 1.

FIG. 2 shows the second section of the overall extraction unit to contain a compression unit 20 that receives butadiene rich vapor stream 15, and subjects it to at least one compression operation, e.g., a compression step followed by heat exchange and liquid separation followed by a second compression step. The thus compressed material from first stripper 10 is introduced by way of line 21 into second reboiled butadiene extractor 22. Lean solvent 23, primary and secondary, is introduced into tower 22 near the top thereof so that, when descending through tower 23 in the same manner described for tower 1 of FIG. 1, it counter currently contacts ascending feed 21.

Tower 22 is operated in such a manner, known in the art, that a butadiene rich overhead 24 is recovered and passed through a conventional reflux circuit composed of a heat exchanger 25 and reflux drum 26. Reflux 27 is split, part being returned by way of line 28 to tower 22, and part being passed by way of line 29 to first reboiled fractionator 30. In distillation column 30, stream 29 is topped and materials lighter than butadiene are removed overhead by line 31 through a conventional reflux circuit (not shown) for ultimate removal from the extraction unit for use elsewhere in the plant, e.g., as fuel. The bottoms of tower 30 are removed by way of line 32 and introduced into reboiled fractionator 33 wherein materials heavier than butadiene are removed as bottoms by way of line 34 for use elsewhere in the plant, e.g., as fuel. The overhead 35 from tower 33 passes through a conventional reflux circuit (not shown) and is then removed as the butadiene product of the olefin plant.

Bottoms 40 of tower 22 contains primarily solvent and tars plus slight amounts of butadiene and acetylenes ($C_3$ and $C_4$), and is passed to a reboiled butadiene recovery column 41. Column 41 typically does not have a reflux circuit for its overhead 42. Overhead 42 is returned directly to line 11 of first stripper 10, and ultimately as a feed material 15 for compression unit 20. Bottoms 43 of column 41 is primarily solvent plus tars and acetylenes, and is passed to second reboiled stripper 44 wherein light materials are stripped from the solvent(s) and tars and recovered overhead for use elsewhere in the plant, e.g., as fuel. Tower 44 typically has a reflux circuit (not shown). Bottoms 46 of tower 44 contains primarily solvent plus tars originally in the solvents and tars formed during the butadiene extraction process, and are recovered for reuse in the butadiene extraction process including the solvent reclamation unit.

Figure 3:
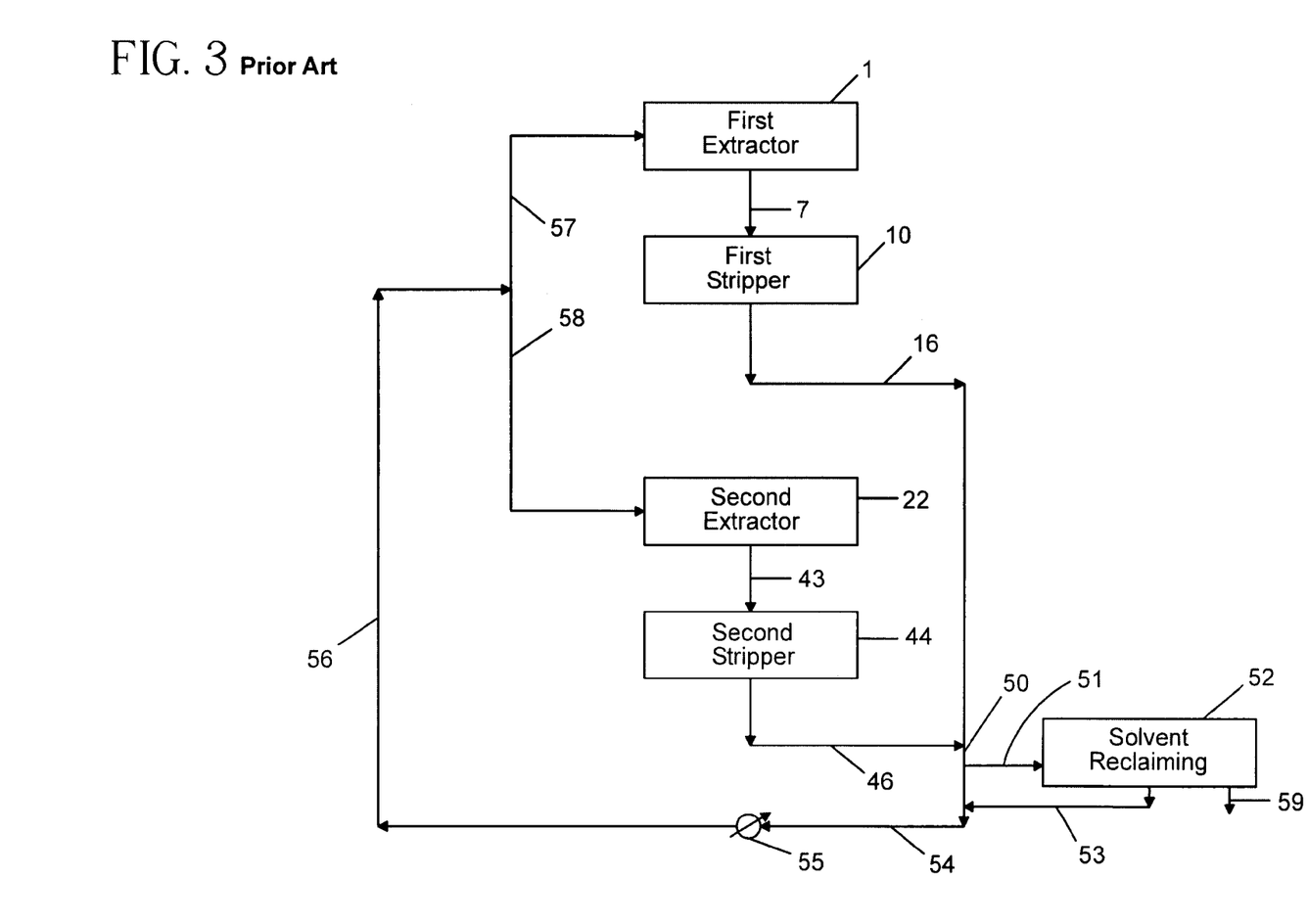
FIG. 3 shows the solvent loop for an extraction plant that contains the extraction circuits shown in FIGS. 1 and 2.

FIG. 3 shows the solvent(s) loop for the extraction process of combined FIGS. 1 and 2. FIG. 3 shows first extractor 1 connected by way of line 7 to first stripper 10, see FIG. 1. FIG. 3 also shows that second extractor 22 is connected (indirectly through column 41) by way of line 43 to second stripper 44, line 40 and column 41 not being shown for sake of clarity. Bottoms 16 of first stripper 10 and bottoms 46 of second stripper 44 are combined into a common stream 50 for reuse as lean solvent in towers 1 and 10 for the extraction of additional butadiene from new feed 2 (FIG. 1).

A minor portion of combined solvent stream 50 is taken as a side stream 51 to be processed for the removal of all or substantially all tars there from in solvent reclaiming unit 52. Solvent essentially devoid of tar is reintroduced into common line 50 by way of line 53. Tar that has been separated from solvent in unit 52 is removed from the process by way of line 59 for other disposition outside the extraction unit. A mixture of recovered solvent carrying tars and reclaimed solvent containing essentially no tars is passed by way of line 54 through at least one heat exchanger 55, and then, by way of line 56, to extractors 1 and 22 for reuse as a lean solvent, stream 56 being split between extractors 1 and 22 by way of lines 57 and 58, respectively. This split between lines 57 and 58 is not necessarily equal, common practice being the majority (more that 50 wt. % based on the total weight of stream of stream 56) going to extractor 1 and the remainder to extractor 10. An 85/15 split is not uncommon.

For sake of clarity, streams 16 and 46, alone or combined, are characterized herein as "primary" mixtures of solvent/tars, e.g., primary lean solvent streams, while streams 51 and 53 are characterized herein as "secondary" mixtures of solvent/tars. Stream 53 is a secondary lean solvent stream that is essentially tar free, and this stream is used to keep the tar level in the overall solvent loop at the desired tar loading.

In the prior art operation of an extraction plant as represented by the combination of FIGS. 1 and 2, the quantity (volume or weight) of secondary side stream 51 taken from primary stream 50 is varied so that after the tars free secondary stream 53 is mixed with the primary stream to form stream 54, the resulting primary stream 54 has essentially the tar content called for by the plant design, e.g., the not less than 2 wt. % tars dictated by the industry prior to this invention. The size of side stream 51 and the amount of tar removed from that side stream in unit 52 before it is added back to the primary solvent stream was used by an operator to meet this 2 wt. % tar goal. The amount of secondary solvent added by way of line 4 (FIG. 1) can be used by an operator to achieve the relative relationship goal of the secondary solvent/tars aforesaid, e.g., secondary solvent 4 plus tars equals 5 wt. %, and also affects the amount of tar free stream 53 that is added to make up stream 54. Thus, it can be seen that, although the control of the overall tar level in the system is easy to state, it is far from easy to achieve in the actual operation of the overall extraction unit. However, operators of such units are skilled, and capable of controlling the unit to essentially meet target tar loading levels. That is why they could heretofore rigorously maintain a 2 wt. % minimum tar loading, and can hereafter maintain a tar loading of not greater than 1.6 wt. %.

Figure 4:
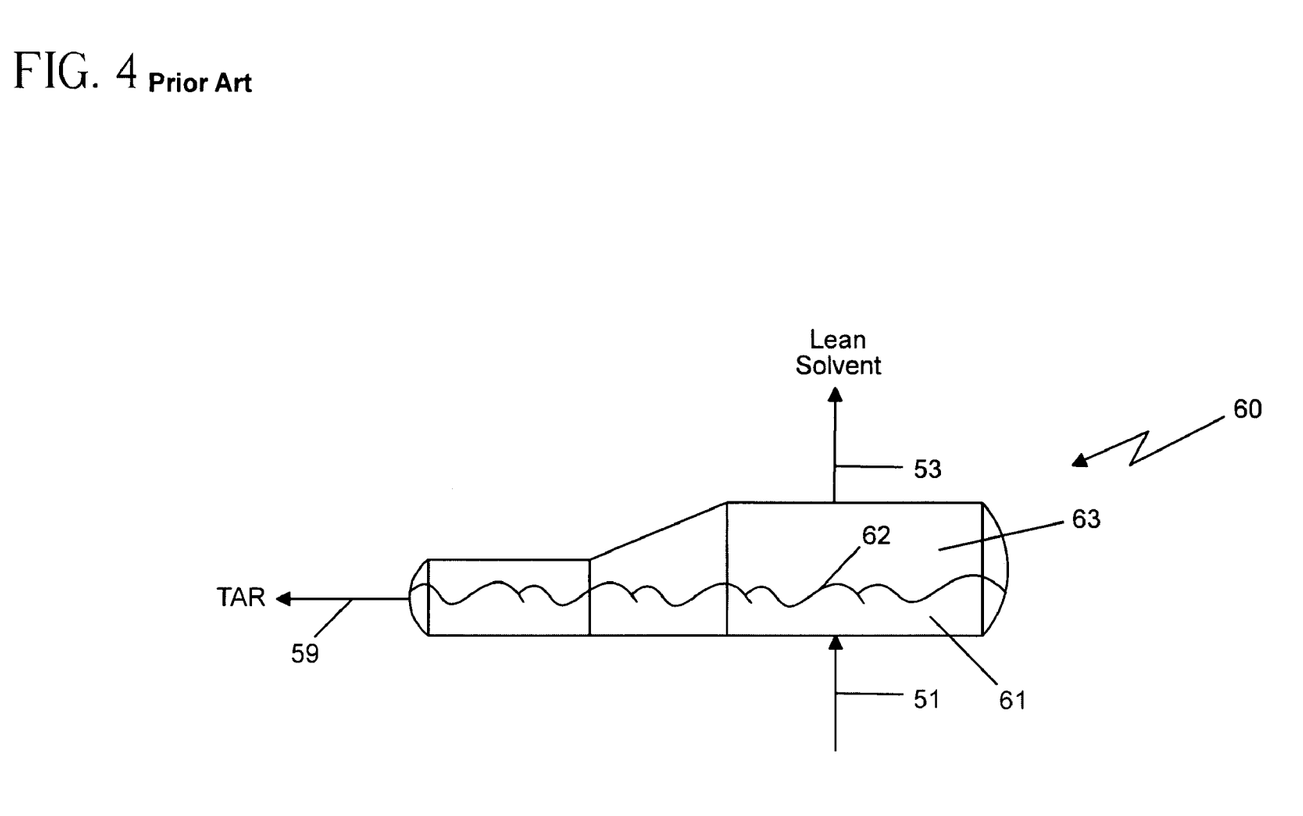
FIG. 4 shows a reboiler that is typically employed in the solvent loop of FIG. 3.

FIG. 4 shows solvent reclaimer 52 of FIG. 3 can be a kettle style reboiler 60. Such devices are well known in the art. Prior art operation of reboiler 60 was to inject hot (about 325° F.) slightly pressurized (about 20 psia) secondary solvent stream 51 into the bottom of reboiler 60 below the tar body therein. Inside reboiler 60 the prevailing pressure is lower than stream 51, e.g., about 5 psia, and solvent is vaporized away from the higher molecular weight tars that are more difficult to vaporize than the solvent(s) present in stream 51. Accordingly, essentially tar free solvent should be recovered overhead in line 54, thereby leaving a build up of tars 61 in reboiler 60. Thus, inside reboiler 60 there is present a mixture 61 of tar, primary solvent, and secondary solvent, if any, which has an upper tar level 62 above which is a vapor space 63 in which only solvent vapor should be present for recovery by way of line 54. When reboiler 60 is operated correctly, the solvent recovered in line 54 should be devoid of tar, i.e., contain essentially no tars.

Although for sake of simplicity it is shown in FIG. 3 that secondary lean solvent 53 is mixed with primary lean solvent 50, lean solvent 53 is commonly collected in a refined solvent receiver (not shown) and reintroduced into the solvent loop of FIG. 3 by employing it as pump seal flush for the various solvent pumps employed in the extraction unit.

Tars in mixture 61 that have been left behind by the vaporizing solvent(s) collect in the lower portion of reboiler 60, and when the amount of tars so collected reaches a target level, e.g., reboiler mixture 61 is from about 30 to about 40 wt. % tar based on the total weight of mixture 61, the collected tars are removed (dumped) from the reboiler and the extraction system by way of line 59. A good measure of the rate of tar generation in a given extractor system is the number of reboiler 60 dumps that have to be made over a given period of time. For example, pursuant to this invention, given the same feed rate for stream 51 and the same overall extraction operating conditions, a 1 wt. % system tar load, based on the total weight of solvent and tar, can result in a reboiler dump about every 5.5 days, whereas a prior art 2 wt. % system tar load can result in a dump about every 3 days.

In the embodiment set forth by FIGS. 1, 2, and 3, solvent reclamation unit 52 was operated by the prior art in accordance with design requirements. This meant that the extraction unit and process was rigorously operated in a manner such that the primary solvent streams 54 through 58, inclusive, carried no less than 2 wt. % tars. This was based on the premise that it took 2 wt. % tars to prevent undesired build up and deposition of tars in the system. When a secondary solvent was employed the prior art operated the extraction process so that not only was the 2 wt. % minimum tar goal maintained, but, also, the total of tars plus secondary solvent in the system was rigorously maintained at no less than 5 wt. %.

It was found that even when maintaining the 2 wt. % tar goal, tars still tended to be generated in the system, i.e., tars begetting tars. The same was true when maintaining a loading of 2 wt. % tars and 3 wt. % secondary solvent.

Pursuant to this invention it was found that by maintaining the tar level at no more than about 1.6 wt. %, surprisingly and unexpectedly, the system became self-cleaning in that tar deposits that were already present inside the equipment before the 1.6 wt. % or less level was established and maintained started to disappear. The same was true when the tar level of this invention was maintained, and the combined tars and secondary solvent level was also maintained at less than 5 wt. %. All wt. % are based on the total weight of the solvent(s) plus tars. It should be noted here that this invention does not include zero percent tars in the solvent(s) employed in the system. Some finite amount of tars should be present in the solvent, it should just be no more than about 1.6 wt. %, preferably less than 1.6 wt. %, still more preferably from a minimum of about 0.1 wt. % to a maximum of less than 1.6 wt. %, all wt. % based on the total weight of the solvent(s) plus tars.

To achieve the lower tar content goal of this invention a larger quantity of secondary stream 51 can be removed for treatment by reboiler 60 in solvent reclamation unit 52 to achieve a consistently larger level of tar removal from the extraction system. In the practice of this invention at least about 0.5 wt. %, desirably, from about 0.5 to about 40 wt. % of primary stream 50 is separated into secondary stream 51, all wt. % based on the total weight of stream 50.

However, it was found that in actual operation, it was not possible to maintain an overall tar content in the system of less than 1.6 wt. % using the apparatus of FIG. 4. The problem was found to reside in the reboiler itself. When hot, slightly pressured stream 51 was injected into tar body 61 of reboiler 60 as shown in FIG. 4, it was found that the flashing of solvent that occurred below surface 62 of the tar body coupled with the increased volume of stream 51 to maintain the overall tar level at no more than 1.6 wt. % caused foaming of tars and intrusion of this foam into vapor space 63. This foaming resulted in undesired, and not heretofore experienced, carryover of tars into the overhead stream 53 which was supposed to be essentially tar free.

In accordance with this invention, stream 51 is cooled before injection of same below tar level 62 to a temperature that prevents flashing of solvent while in the tars below level 62, thereby preventing foaming and carryover of tars into stream 53. Accordingly, in this embodiment of the invention the temperature of input feed 51 should be no higher than from about 160 to about 180° F.

Figure 5:
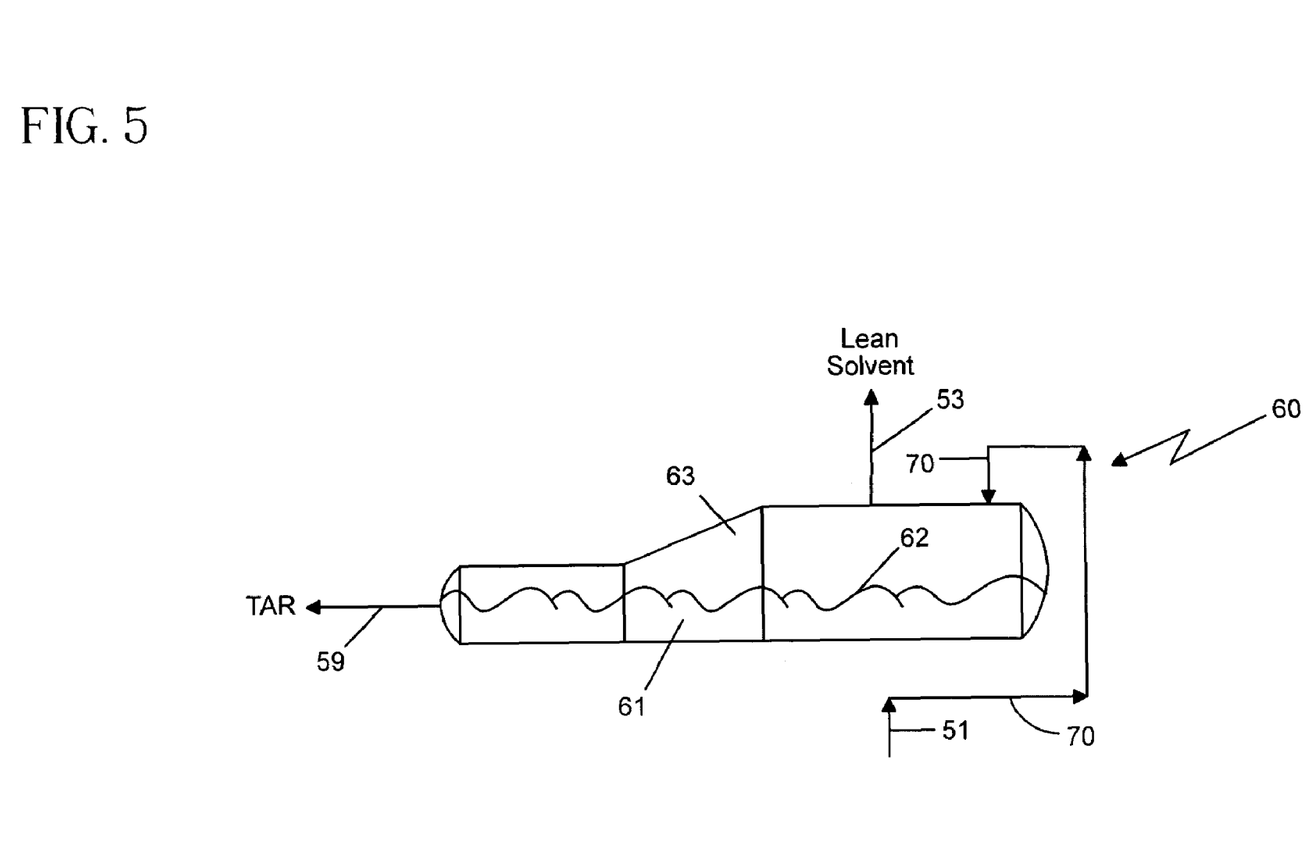
FIG. 5 shows the reboiler of FIG. 4 modified to operate in accordance with one embodiment of this invention.

Other solutions will become apparent to those skilled in the art once appraised of this invention, and they are considered to be part of this invention. For example, FIG. 5 illustrates one such alternative solution. FIG. 5 shows the same apparatus as FIG. 4 except that stream 51 has been rerouted by way of line 70 to introduce stream 51 into the vapor space 63 that exists inside reboiler 60 above tar level 62. In this embodiment, hot, slightly pressured stream 51 need not be cooled, and can be injected into vapor space 63 with no worry of tar carryover into stream 53 because the solvent in stream 51 flashes in vapor space 63 and not inside tar body 61 under surface 62 with no resultant foaming. Of course, a combination of cooler feed to the bottom of reboiler 60 and hotter feed to the vapor space in reboiler 60 can be employed.

The solvents employed in this invention can be the same as employed by the prior art discussed hereinabove. Dimethylformamide (DMF) and furfural are particularly effective, although others can be used in this invention. When DMF and furfural are employed together, it is presently preferred that DMF be employed in major amount with furfural the minority remainder, e.g., DMF at least about 90 wt. % and furfural less than about 10 wt. %, both based on the total weight of DMF and furfural combined. When a mixture of two solvents is employed, the secondary solvent can be present in an amount of from about 0.1 wt. % to about 3.0 wt. %, based of the total weight of the mixture.

Normal operation of any butadiene extraction unit inherently generates long chains of $C_4$ compounds no matter how the process is carried out. These long chains are polymers (tars) that have been formed from monomers such as butadiene, vinyl acetylene, furfural, and the like. These polymers can be homopolymers, e.g., polybutadiene, or copolymers, e.g., copolymers of butadiene and vinyl acetylene. These polymers grow from lower molecular weight (lighter and relatively more volatile) to higher molecular weight (heavier and less volatile) the longer they reside in the extraction system. Generally, relative to the $C_4$'s present, they are heavier molecular weight materials. These polymers vary from those that resist volatilization under the various temperature and pressure conditions that prevail in the normal operation of a butadiene extraction unit up to those that simply will not volatilize under any of the prevailing conditions of temperature and pressure throughout the extraction unit, the lower molecular weight polymers simply being those that are on their way to becoming higher molecular weight polymers upon continued exposure to the operating conditions prevailing in the extraction unit. Thus, these polymers are difficult, if not impossible, to quantify further, but functional description of these materials is sufficient to inform the art because they are so prevalent in extraction processes. The conventional test procedure for determining the amount of tars that simply will not volatilize and that are present in a fluid such as a lean solvent that is to be used in an extractor is to heat a sample of such fluid at 212° F. and 28 inches of mercury pressure for 2 hours. The non-volatiles that remain constitute the tar fraction of the sample. The tars referred to in describing this invention can include both lighter and heavier molecular weight materials, and thus are not strictly limited to tars as determined by the foregoing test procedure.

Based on the practice of this invention a number of advantages arise over the prior art practice. First, there is an increased time of continuous operation between extractor unit shutdowns for cleaning and maintenance, and essentially no such shutdowns based on tar deposition. This saves substantially on maintenance costs and lost production. Reboilers 6 and 17, and solvent heat exchangers 55 are the first to show signs of plugging due to tar deposition. After that the various towers themselves can be subject to tar deposition and potential plugging. This invention substantially reduces, if not eliminates the need for cleaning tar deposits out of such equipment. When operating under the reduced tar free environment of this invention, particularly as to tar deposits, energy costs are reduced. Finally, less solvent is lost from the reclamation unit.

EXAMPLE 1

An extraction unit as depicted in FIGS. 1 through 4 was operated using a crude $C_4$ feedstock 2 for extractor 1 that contained about 6.8 wt. % n-butane, about 1.3 wt. % isobutane, about 13.5 wt. % 1-butene, about 10.3 wt. % 2-butenes (cis and trans), about 27.9 wt. % isobutylene, about 39.5 wt. % butadiene (1,2 and 1,3), about 0.5 wt. % vinyl acetylene, and about 0.1 wt. % ethyl acetylene, all wt. % being based on the total weight of the feed. Feed 2 was introduced into extractor 1 at a temperature of about 125° F. at about 65 psig, and a flow rate of about 60,000 pounds per hour (pph).

The extraction process employed dimethylformamide as the primary solvent and furfural as the secondary solvent. The total weight of the combined solvents, including a tar load of 2 wt. %, contained about 95 wt. % primary solvent and about 3 wt. % secondary solvent. The solvents were introduced into extractor 1 at a temperature of about 104° F. at about 48 psig, and a flow rate of about 415,000 pph.

Extractor 1 was operated with a bottom temperature of about 260° F. at 80 psig, and an overhead temperature of about 110° F. at about 50 psig with an external reflux rate of about 45,000 pph. Extractor 1 produced about 35,000 pph of raffinate ($C_4$'s essentially free of butadiene) at about 110° F. Butadiene rich solvent was removed as bottoms 7 at a flow rate of about 351,000 pph and passed to first stripper 10.

Stripper 10 had a bottom temperature of about 335° F. at about 6 psig, and a reflux rate in line 14 of about 45 gallons per minute (gpm). About 60,000 pph of butadiene rich gas 15 was removed from reflux drum 13 and passed to compression unit 20. About 30,000 pph of gas 15 was passed from compression unit 20 to second extractor 22. About 415,000 pph of combined solvent and tars was removed as bottoms 16 and sent to reboiler 60. Bottoms 16 was at about 335° F. at 6 psig.

Compression unit 20 employed a two stage compression process with heat exchange cooling between the two compression steps. Solvent at about 91° F. and about 90 psig was removed from unit 20 and passed to second extractor 22 at the flow rate of about 30,000 pph.

Extractor 22 was operated at a bottom temperature of about 258° F. at about 48 psig, a top temperature of about 110° F. at 50 psig, and a reflux rate of about 30,000 pph. Bottoms 40 of extractor 22 was removed at a rate of about 50,000 pph and sent to butadiene removal column 41.

Column 41 was operated at a bottom temperature of about 260° F. at about 5 psig. Overhead 42, at about 210° F. and 5 psig, was sent to first stripper 10 at a flow rate of about 3,000 pph. Bottoms 43, at a flow rate of about 47,000 pph, was sent to second stripper 44.

Second stripper 44 was operated at a bottom temperature of about 325° F. at 3.5 psig using a reflux rate of about 12 gpm. Bottoms 46 was sent to reboiler 60 at the flow rate of about 45,000 pph. Overhead 45 removed from the extraction unit.

Overhead 24 of extractor 22 was sent by way of line 29 to first fractionator 30 at the rate of about 27,000 pph. Tower 30 was operated with a bottom temperature of about 116° F. at about 53 psig overhead under total reflux. Bottoms 32 was passed to second fractionator 33 for final separation of butadiene product from the remaining solvent. Tower 33 was operated at a bottom temperature of about 140° F. at 70 psig, with a reflux rate of about 180,000 pph. Final butadiene product was removed by way of overhead stream 35 at the rate of about 26,000 pph. Bottoms 34 was removed from the extraction process.

Reboiler 60 was maintained at a temperature of about 190° F. at about minus 9 psig (5 psia). Feed 51 (combined from bottoms 16 of stripper 10 and bottoms 46 of stripper 44) was passed into reboiler 60 at a temperature of about 325° F. at about 5 psig (20 psia) at the rate of about 1,700 pph. The tar content of stream 51 was about 2 wt. % based on the weight of stream 51, the remainder being DMF (about 95 wt. %) and furfural (about 3 wt. %), all wt. % based on the total weight of stream 51. The secondary solvent (furfural) plus the tar level was about 5 wt. % based on the weight of stream 51. At this tar level reboiler 60 required emptying over 9 times per month.

When operating under the conditions of this Example 1, the longest the extraction unit, as a whole, was operated continuously before shut down was required for tar clean out was 31.7 months.

EXAMPLE 2

The operation of Example 1 was repeated except that the flow rate of stream 5 to reboiler 60 was increased to about 2,100 pph (a 23.5% increase), and the temperature of stream 51 reduced to about 170° F. at a pressure of minus 10 psig (4.7 psia).

After operating under these conditions for an extended time sufficient to stabilize the extraction system as a whole, the tar content of stream 51 had fallen to about 1 wt. % based on the weight of stream 51, and the secondary solvent plus tar level had fallen to less than 5 wt. % based on the weight of stream 51.

Continued operation of the extraction unit as a whole at this reduced tar loading required emptying of reboiler 60 only 7 times per month in order to maintain the 1% tar loading even though the feed rate of stream 51 had been increased 23.5%.

In addition, while operating under this reduced tar level, about 25% less primary solvent was used and the extraction unit experienced a self-cleaning effect in that previous tar deposits were later found to be reduced in volume. The extraction system as a whole experienced less tar fouling in its equipment, particularly the first to foul heat exchangers 6 (e.g., one steam reboiler and up to two solvent reboilers) and 17. This resulted in significantly reduced extraction unit steam usage and cost.

Additional benefits found with the practice of this invention pursuant to this Example 2 were an increase in extractive unit operating capacity, as evidenced by an ability to operate the unit at a higher input rate for $C_4$ feed 2, and a decreased energy cost—3,100 btu/pound of butadiene product for Example 2 versus 4,400 btu/pound of butadiene for Example 1.

While operating under the conditions of this Example 2, the extraction unit was run continuously for 47 months without need for shut down for polymer (tar) clean out. At 47 months the olefin production plant as a whole was shut down for a regularly scheduled turnaround. During this turnaround, upon internal inspection by experienced personnel, it was found that the upper section of extractor 1 was cleaner of tar than at the end of a prior 32 month run using a 2 wt. % minimum tar loading, hence the self-cleaning advantage.

Also, at the 47 month shut down, the lower section of extractor 1 was scheduled to have its trays removed and cleaned, which was previously under prior art operation necessary. However, due to the limited nature of tar deposition found on the trays, they were merely cleaned by hand in place in the tower. This alone saved substantial maintenance time and expense.

Based on the substantially reduced polymer deposits actually found in the extraction unit equipment, it was projected that the unit could have run for 60 months without need of a shut down for polymer clean up. A 60 month continuous run time for the unit would mean that the unit could match the run time for the olefin production plant as a whole.

This Example 2 demonstrates that this invention not only lowers the rate of tar formation in the extraction process as a whole, but, also, has a self-cleaning effect on equipment that has already experienced polymer deposition.

We claim:

1. In a process for the solvent extraction of butadiene from a mixture of $C_4$ compounds that boil close to butadiene and the recovery of butadiene as a product of the process, wherein at least one solvent extraction step is employed using at least one lean solvent that preferentially extracts butadiene from said mixture of $C_4$'S to form a solvent extract stream that carries butadiene and tars that form during said butadiene extraction process, said extract being subjected to a stripping operation to separate butadiene from said solvent and tars, the butadiene separated from said solvent and tars being recovered as a product of the process, a separate primary mixture of solvent and tars being recovered for reuse in said at least one solvent extraction step, and wherein a secondary portion of said primary mixture of solvent and tars is separated from said primary mixture and subjected to a reclamation step in which substantial quantities of tars are removed from said secondary portion and from said extraction process thereby forming a secondary lean solvent stream that is essentially depleted in its content of tars, and reintroducing said secondary lean solvent stream into said extraction process to absorb additional butadiene, the improvement comprising operating said extraction process in a manner such that sufficient tars are removed from said extraction process to maintain the amount of tars present in said extraction process at a level no greater than about 1.6 wt. %, based on the total weight of solvent and tars in said extraction process.

2. The method of claim 1 wherein two solvents are employed in said extraction process, the first of said solvents being employed in a major amount and the second of said solvents being employed in a minor amount, said extraction process including said reclamation step is operated in a manner to maintain the total amount of secondary solvent and tars in said extraction process at a level of less than 5 wt. % based on the total weight of both solvents and tars in said extraction process.

3. The method of claim 1 wherein said reclamation step employs at least one reboiler with an overhead vapor condenser system in which solvent is boiled as vapor overhead from said tars and condensed to an essentially tar free liquid for reintroduction into said extraction process and tars are left in said reboiler for separate removal from said extraction process, said tars in said reboiler having an upper level in said reboiler above which is vapor space, said reboiler being operated in a manner such that said tar laden secondary portion solvent feed to said reboiler is at least one of 1) introduced into said reboiler below said tar level at a temperature sufficient to prevent foaming in said reboiler, and 2) introduced into said reboiler vapor space above said tar level.

4. The method of claim 3 wherein said tar laden solvent introduced below said tar level is sufficiently cool to essentially avoid flashing of said solvent while below said tar level.

5. The method of claim 3 wherein said tar laden solvent introduced above said tar level is heated to a temperature that can cause at least some flashing of said solvent while it is in said vapor space above said tar level.

6. The method of claim 2 wherein two solvent extractors are employed each associated with stripper units for separating tar laden solvent for reuse in said extraction process including said reclamation step, the primary mixture of solvent and tars from each of said associated strippers being combined to form a single primary mixture of solvent and tars, and a secondary portion of said single primary mixture is split off there from for tar separation in said reclamation step.

7. The method of claim 6 wherein said reclamation step employs at least one kettle reboiler with an overhead condenser system in which solvent is boiled as vapor overhead from said tars and condensed to liquid for reintroduction into said extraction process and tars are left in said reboiler for separate removal from said extraction process, said tars in said reboiler having an upper level above which is vapor space, said reboiler being operated in a manner such that tar laden secondary portion solvent feed to said reboiler is at least one of 1) introduced into said reboiler below said tar level at a temperature sufficient to prevent solvent/tar foaming in said reboiler and consequent carryover of tars into said overhead, and 2) introduced into said reboiler in said vapor space above said tar level.

8. The method of claim 2 wherein said solvents are dimethylformamide and furfural, said dimethylformamide being present in an amount greater than about 90 wt. %, and said furfural being present in an amount less than about 10 wt. %, both wt. % being based on the combined total weight of both solvents and tars, and essentially all tars are removed from said secondary portion of said primary mixture of solvents and tars before said reclaimed solvent is reintroduced into said extraction process.

9. The method of claim 8 wherein said secondary portion of said primary mixture of solvent and tars is from about 0.1 wt. % to about 1.6 wt. % of said primary mixture based on the total weight of said primary mixture.

10. The method of claim 9 wherein said extraction process including said reclamation step is operated so as to maintain in said extraction process both 1) the amount of tars at a level of less than 1.6 wt. %, and 2) the total amount of tars and secondary solvent at a level of less than 5 wt. %, all wt. % being based on the total weight of solvents and tars in said extraction process.

11. The method of claim 1 wherein said tars are polymers formed from said $C_4$ compounds, said polymers being not readily vaporizable under the operating conditions of temperature and pressure of said extraction process.

* * * * *